United States Patent
Lupien et al.

(10) Patent No.: US 9,382,588 B2
(45) Date of Patent: Jul. 5, 2016

(54) MARKERS FOR IDENTIFYING BREAST CANCER TREATMENT MODALITIES

(75) Inventors: Mathieu Lupien, Toronto (CA); Luca Magnani, London (GB)

(73) Assignee: Trustees of Dartmouth College, Hanover, NH (US)

( * ) Notice: Subject to any disclaimer, the term of this patent is extended or adjusted under 35 U.S.C. 154(b) by 324 days.

(21) Appl. No.: 13/985,470

(22) PCT Filed: Feb. 15, 2012

(86) PCT No.: PCT/US2012/025183
§ 371 (c)(1),
(2), (4) Date: Sep. 23, 2013

(87) PCT Pub. No.: WO2012/112645
PCT Pub. Date: Aug. 23, 2012

(65) Prior Publication Data
US 2014/0011695 A1    Jan. 9, 2014

Related U.S. Application Data

(60) Provisional application No. 61/443,813, filed on Feb. 17, 2011, provisional application No. 61/593,461, filed on Feb. 1, 2012.

(51) Int. Cl.
*C12Q 1/68* (2006.01)
*C07K 16/30* (2006.01)
*G01N 33/574* (2006.01)

(52) U.S. Cl.
CPC .......... *C12Q 1/6886* (2013.01); *C07K 16/3015* (2013.01); *G01N 33/57496* (2013.01)

(58) Field of Classification Search
None
See application file for complete search history.

(56) References Cited

U.S. PATENT DOCUMENTS

| | | | |
|---|---|---|---|
| 2008/0207714 A1 | 8/2008 | Chinnaiyan et al. | 514/381 |
| 2009/0222387 A1 | 9/2009 | Gehrmann et al. | 706/12 |
| 2009/0239223 A1 | 9/2009 | Gehrmann et al. | 435/5 |
| 2010/0311601 A1 | 12/2010 | Symmans et al. | 506/8 |
| 2011/0014191 A1 | 1/2011 | Bertucci et al. | 424/133.1 |

FOREIGN PATENT DOCUMENTS

WO  PCT/US2012/025183   5/2012
WO  PCT/US2012/025183   8/2013

OTHER PUBLICATIONS

Carroll et al. "Chromosome-Wide Mapping of Estrogen Receptor Binding Reveals Long-Range Regulation Requiring the Forkhead Protein FoxA1" Cell 2005 122:33-43.
Fernandez et al. "Oncogenic HoxB7 Requires Tale Cofactors and Is Inactivated by a Dominant-Negative Pbxl Mutant in a Cell-Specific Manner" Cancer Letters 2008 266:144-155.
Johnston, S.R.D. "New Strategies in Estrogen Receptor-Positive Breast Cancer" Clinical Cancer Research 2010 16(7):1979-1987.
Lupien et al. "Growth Factor Stimulation Induces a Distinct ER∝ Cistrome Underlying Breast Cancer Endocrine Resistance" Genes & Development 2010 24:2219-2227.
Park et al. "Identification of Pbxl, a Potential Oncogene, as a Notch3 Target Gene in Ovarian Cancer" Cancer Research 2008 68(21):8852-8860.
Shou et al. "Mechanisms of Tamoxifen Resistance: Increased Estrogen Receptor-HER2/neu Cross-Talk in ER/HER2-Positive Breast Cancer" Journal of the National Cancer Institute 2004 96(12):926-935.
Sørlie et al. "Gene Expression Patterns of Breast Carcinomas Distinguish Tumor Subclasses with Clinical Implications" Proceedings of the National Academy of Sciences 2001 98(19):10869-10874.
Svingen, T. and Tonissen, K.F. "Altered HOX Gene Expression in Human Skin and Breast Cancer Cells" Cancer Biology & Therapy 2003 2(5):518-523.
Swanton, C. and Downward, J. "Unraveling the Complexity of Endocrine Resistance in Breast Cancer by Functional Genomics" Cancer Cell 2008 13:83-85.
Xiao et al. "The Lymphovascular Embolus of Inflammatory Breast Cancer Exhibits a Notch 3 Addiction" Oncogene 2011 30:287-300.

*Primary Examiner* — Jim Ketter
(74) *Attorney, Agent, or Firm* — Licata & Tyrrell P.C.

(57) ABSTRACT

The present invention includes methods for identifying patients who will be resistant to endocrine therapy during breast cancer treatment and determining patient outcome. The methods are based on identifying increased expression of PBX1, or the cistrome signature associated therewith, in breast tissue samples.

1 Claim, 2 Drawing Sheets

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1
gaggaagcag gacattggag                                          20

<210> SEQ ID NO 2
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2
aggcttcatt ctgtggcagt                                          20
```

MARKERS FOR IDENTIFYING BREAST CANCER TREATMENT MODALITIES

This patent application is a U.S. National Stage Application of PCT/US2012/025183 filed Feb. 15, 2012 and claims the benefit of priority from U.S. Provisional Application Ser. No. 61/443,813 filed Feb. 17, 2011 and from U.S. Provisional Application Ser. No. 61/593,461 filed Feb. 1, 2012, the contents of each of which are herein incorporated by reference in their entirety.

BACKGROUND OF THE INVENTION

Breast cancer is the most frequently diagnosed cancer and the second most common cause of cancer death in women. While endocrine therapies have proven to be initially effective, almost half of breast cancer patients eventually present recurrent tumors that are resistant to these therapies. The reasons behind endocrine therapy resistance remain poorly understood, and as a consequence there are no prognostic markers or therapeutic alternatives with which to treat these patients.

Estrogen receptor alpha (ERα) is involved in the pathogenesis of over 70% of all breast cancers, and plays a role as both a therapeutic target and prognostic factor (Sorlie, T. et al. 2001. *Proc. Natl. Acad. Sci. USA* 98:10869-10874). The receptor stimulates cell proliferation by binding DNA at regulatory elements in response to a diverse number of stimuli such as estrogens and growth factors (Carroll, J. S. et al. 2005. *Cell* 122:33-43). Currently, the main therapeutic strategies for treatment of breast cancer consist of modulating ERα activity by antagonizing its endogenous ligand (i.e., estrogen) with a selective estrogen receptor modulator (SERM) such as tamoxifen, or by inhibiting aromatase-driven estrogen synthesis (aromatase inhibitor). Unfortunately, all patients with ERα-positive metastatic breast cancer and half or more of ERα-positive early stage breast cancers will develop resistance to endocrine therapy (Swanton, C. and J. Downward. 2008. *Cancer Cell* 13:83-85).

Growing evidence suggests that growth factor pathways, which activate ERα independently from estrogen, may be involved in the development of drug resistance in breast cancer. HER2, an epidermal growth factor family receptor, has clearly been linked to the development of endocrine therapy resistance in breast cancer (Shou, J. et al. 2004. *J. Natl. Cancer Inst.* 96:926-935). Recent studies support a role for the epidermal growth factor receptor (EGFR) in breast cancer (Johnston, S. R. 2010. *Clin. Cancer Res.* 16:1979-1987). Epidermal growth factor (EGF) has been shown to induces a distinct ERα genome-wide DNA binding profile (known as its cistrome) compared to estrogen in breast cancer cells (Lupien, M. et al. 2010. *Genes Dev.* 24:2219-2227). More importantly, while the estrogen-ERαcistrome is associated with genes of the ERα-positive, or projected good prognosis signature of breast cancer, the EGF-ERα cistrome defines a subset of genes associated with HER2 and poor prognosis signature (Lupien, M. et al. 2010. *Genes Dev.* 24:2219-2227). Furthermore, EGF-ERα mediated tumor cell growth is not responsive to tamoxifen treatment (Lupien, M. et al. 2010. *Genes Dev.* 24:2219-2227). These data suggest that EGF-induced ERα activation is central in the development of endocrine therapy resistance in ERα-positive breast cancers. Unfortunately, there are no predictive markers for response to endocrine therapy in ERα-positive breast cancers.

U.S. Patent Application Nos. 2008/0207714, 2009/0222387, and 2009/0239223) disclose methods for diagnosing or treating breast cancer (2008/0207714 and 2009/0222387), or a method for predicting breast cancer response to taxane-based chemotherapy (2009/0239223). PBX1 is listed in these patents as one of a group of genes that might be involved in carcinogenesis, yet none of the applications disclose use of PBX1 as a novel marker for breast cancer or drug treatment of breast cancer.

Svingen and Tonissen (2003. *Cancer Biol. Ther.* 2:518-523) teach that human HOX genes are expressed in breast cancer cells in vitro, and included measurement of the HOX co-factor PBX1. Although HOX genes were shown to be specifically dysregulated in malignant breast cancer cells, the co-factor PBX1 was not dysregulated. The authors concluded that HOX genes, but not the co-factor PBX1, commit cancer cells to re-differentiate and undergo oncogenic transformation.

Fernandez et al. (2008. *Cancer Lett.* 266:144-155) disclose that PBX1 plays a role in HoxB7 oncogenic activity in breast cancer cells in vitro. The authors show that in SkBr3/B7 cells, a type of breast cancer cell, HoxB7 is important in the tumorigenic process.

Xiao et al. (2010. *Oncogene* Epub September 13) disclose that the Notch3 gene is activated in a model of inflammatory breast carcinoma. Upregulation of Notch3 was shown to lead to increased expression of several downstream targets including PBX1.

SUMMARY OF THE INVENTION

The present invention is a method of identifying patients resistant to breast cancer endocrine therapy by determining a level of expression of PBX1 in vitro in a ERα-positive breast cancer tissue sample; and comparing the level of expression of PBX1 in the breast cancer tissue sample with the level of expression of PBX1 in a control sample, wherein greater levels of PBX1 in the ERα-positive breast cancer tissue sample as compared to the control sample is indicative of resistance to endocrine therapy in a patient.

The present invention is also a method for determining the outcome of a patient with breast cancer by assaying a sample of breast cancer cells from a subject with breast cancer for the expression levels of one or more genes of Table 1; and comparing said expression levels with the expression levels of the one or more genes of Table 1 in a control sample, wherein greater levels of the one or more genes of Table 1 in the breast cancer tissue sample as compared to the control sample is indicative of an unfavorable outcome. In certain embodiments of this method, outcome is metastasis, recurrence, or survival and is indicative of responsive to endocrine therapy treatment. A kit for determining outcome of a patient with breast cancer is also provided.

DETAILED DESCRIPTION OF THE INVENTION

ERα activity is, in part, dependent on the pioneer factor FoxA1 that translates epigenetic cues to functional binding (Lupien, M. et al. 2008.*Cell* 132:958-970). A novel ERα-associated pioneer factor known as pre-B-cell leukemia homeobox-1 or PBX1 has now been identified. In the context of the present invention PBX1 is a "pioneer factor", where this term is defined as a factor that can integrate condensed chromatin and render it accessible to transcription factors. Data have demonstrated that the PBX1 motif is highly enriched in the EGF-ERα cistrome, indicating that this factor plays a role in promoting ERα response to EGF. Consequently, PBX1 and the genes affected by the activity of PBX1, are ideal markers to discriminate response to endocrine therapies in ERα-positive breast cancer, including the use of compounds that would include but not be limited to selective estrogen receptor modulators and aromatase inhibitors. Thus, the present invention is a method of determining what type of breast cancer treatment method will be successfully used in a patient diagnosed with breast cancer.

Figure 1:
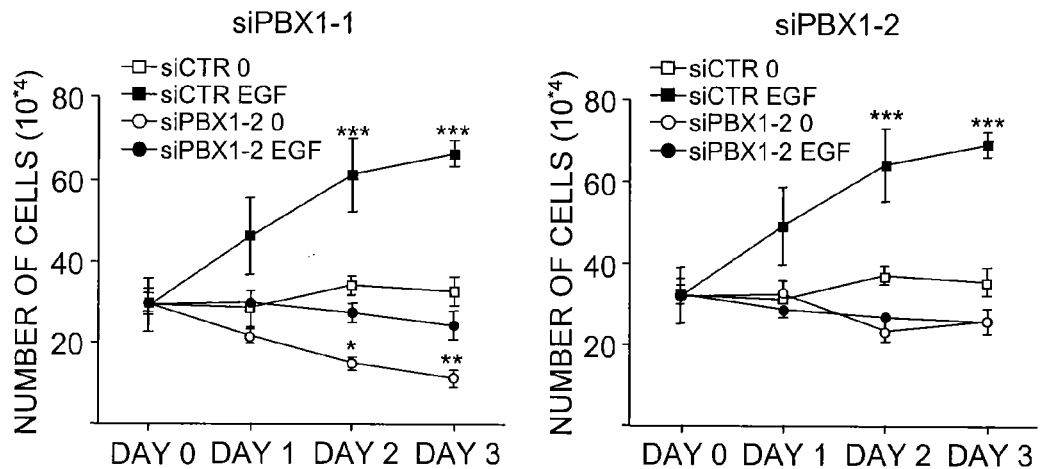
FIG. 1 depicts results of experiments showing that MCF7 cells depleted of PBX1 do not grow in response to EGF.

Experiments were first performed to examine the role of PBX1 as a key regulator of the growth factor pathway-ERα pathway that is involved in breast cancer and targeted during breast cancer treatment. It has been found that PBX1 regulates ERα activity and is necessary to promote EGF induced transcription and cell growth (FIG. 1). It has also been found that PBX1 expression in primary breast tumors correlates with ERα, data that indicates there is a functional connection. These data were collected in a series of biological assays on cells depleted of PBX1 using siRNA.

Figure 2:
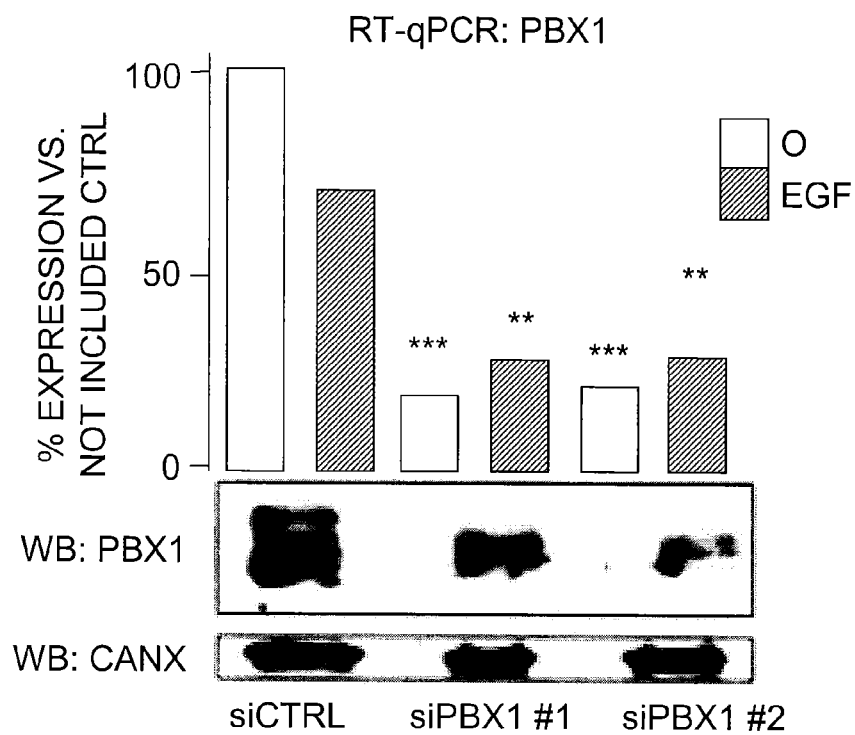
FIG. 2 depicts results of experiments showing mRNA and protein levels for PBX1 following siRNA transfection with two independent siRNA against PBX1 and the comparison to a negative control siRNA. Calnexin (CANX) was used as a control for protein level.
Figure 3:
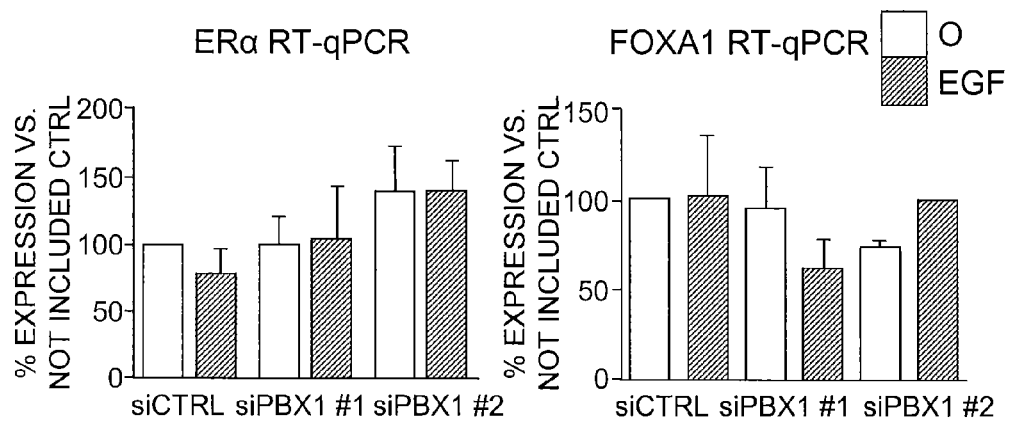
FIG. 3 depicts results of experiments showing that PBX1 depletion does not affect ERα or FOXA1 mRNA levels.
Figure 4:
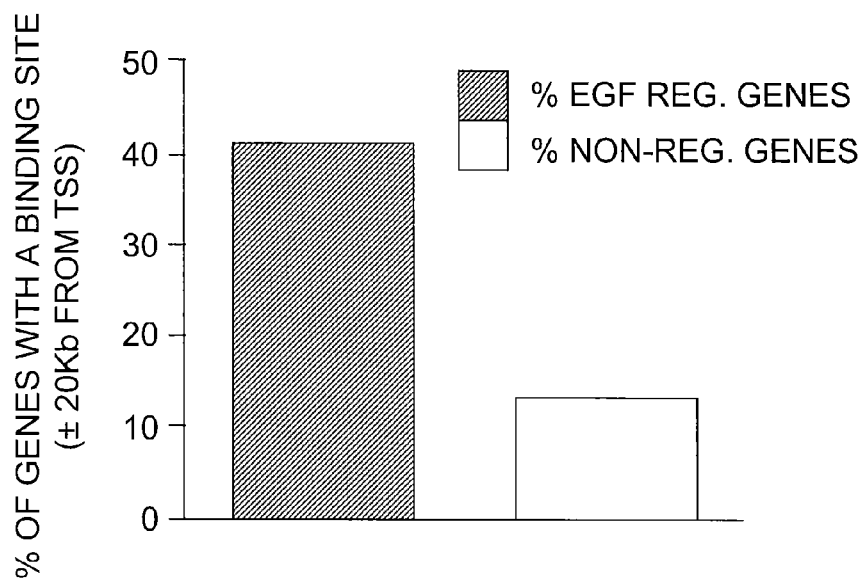
FIG. 4 depicts results of experiments showing that PBX1 motif overlapping EGF-ERα cistrome significantly relates to EGF regulated genes ($p<3*10^{-23}$, Fisher's exact test).

Depletion of PBX1 via siRNA decreased mRNA expression of key EGF-induced ERα target genes in MCF7 cells, while not affecting ERα or FoxA1 expression (FIGS. 2 and 3). Supporting these findings that PBX1 plays an integral role in functioning of endocrine responses in breast cancer, ChIP-qPCR assays demonstrated that PBX1 occupies the chromatin at EGF-ERα binding sites prior to ERα recruitment. In agreement, the DNA motif recognized by PBX1 was present in 90% of the EGF-ERα cistrome. In fact, EGF-ERα binding sites harboring the DNA motif recognized by PBX1 were highly enriched at regulatory elements related to EGF regulated genes (FIG. 4), further supporting the role of PBX1 in driving a transcriptional response relevant to endocrine therapy resistance in breast cancer. Considered together, these data demonstrated that PBX1 and ERα collaborate to promote EGF mediated cell growth permissive to endocrine therapy resistance in breast cancer.

To assess the capacity of PBX1 to alter chromatin structure and increase DNA accessibility Formaldehyde-Assisted Isolation of Regulatory Elements (FAIRE) assays were performed (Zaret, K. S. et al. 2008. *Cold Spring Harb. Symp. Quant. Biol.* 73:119-126). The results of these assays demonstrated that PBX1 depletion leads to chromatin condensation at ERα binding sites, validating its role as a pioneer factor in breast cancer.

ERα status is a decisive factor in selecting therapeutic strategies for breast cancer patients. To date, ERα is the most exploited marker in the clinic and generally associates with good outcomes (Payne, S. J. et al. 2008. *Histopathology* 52:82-90), but unfortunately, the mere presence of ERα does not unfailingly predict response to endocrine therapies since many cancers recur or progress despite the fact that patients continue to express high levels of ERα. Thus, experiments were performed to assess the diagnostic and prognostic potential of PBX1 in ERα-positive breast cancers.

Clinical samples of primary breast tumors and ERα-positive MCF7 breast cancer cells were tested for the expression of PBX1 mRNA. Results showed that high expression of PBX1 was found in both sample types tested. Kaplan-Meier curves generated through a meta-analysis comparing ERα-positive breast cancer with high versus low PBX1 mRNA expression demonstrates that high-PBX1 expression is associated with a decreased metastasis and most importantly a decreased recurrence-free survival.

Considering that ERα-positive breast cancer patients are commonly treated with endocrine therapy at the time of diagnosis, recurrence-free survival corresponds to resistance-free survival.

The results herein demonstrate that PBX1 expression in ERα primary breast cancers correlates with recurrence. It has been observed that the culture of ERαpositive sensitive cell lines (>1 year) in the absence of estradiol produces long-term estrogen-deprived (LTED) cells that have become resistant to all the endocrine therapies currently available. Hence, to recapitulate in vitro the molecular mechanisms that lead to endocrine therapy resistant, parental sensitive cells (MCF-7, ZR75 and T47D) and ETR (LTED cells) were employed. These models indicate a gradual change in response to aromatase inhibitors. Indeed, genes highly expressed in LTED cells are significantly associated with poor outcome breast cancer (high-grade tumors). Conversely, MCF-7-genes are associated with genes under-expressed in high-grade cancers. These data demonstrate that LTED cells have become transcriptionally distinct from the MCF-7 parental line and indicate that a shift has occurred at the epigenetic level.

Cell type identity is characterized by a collection of epigenetically marked regulatory elements such as functional enhancers. Results indicate that MCF-7 and LTED cells are epigenetically different at these regions for the enhancer-specific marker H3K4me2. Notably, pioneer factor proteins contribute to the deposition and translation of these epigenetic modifications, promoting open chromatin structure for subsequent transcription factors binding.

As demonstrated herein, the pioneer factor PBX1 is specifically over-expressed in ERα positive breast cancer and PBX1 expression in ERα primary breast cancers correlates with recurrence. In agreement, PBX1 controls two distinct subsets of genes in the sensitive (MCF-7) and resistant cells (LTED). More importantly, it is the specific LTED PBX1-dependent component (495 genes) that contributes to over fifty poor outcome independent gene signatures (recurrence/metastasis/death) as established using ONCOMINE. On the other hand, PBX1-dependent genes in MCF-7 are only marginally associated with poor outcome. These results suggest that PBX1 binding-shift drives the global chromatin landscape re-arrangement underlying transcriptional changes during ETR development connected to poor outcome.

As indicated, 495 PBX-dependent genes were identified in LTED cells. Of these, a predictive gene list, based on 25 candidates, was derived (Table 1).

TABLE 1

| Gene Symbol | Gene Name | GENBANK Accession No. |
| --- | --- | --- |
| AURKA | Aurora kinase A | NM_003600 |
| AURKB | Aurora kinase B | NM_004217 |
| BUB1 | BUB1 budding uninhibited by benzimidazoles 1 | NM_004336 |
| CCNB1 | Cyclin B1 | AA632161 |
| CDCA3 | Cell division cycle associated 3 | AI934517 |
| CDKN3 | Cyclin-dependent kinase inhibitor 3 | NM_005192 |
| CEP55 | Centrosomal protein 55 kDa | NM_018131 |
| DLGAP5 | Discs, large (*Drosophila*) homolog-associated protein 5 | NM_014750 |
| FEN1 | Flap structure-specific endonuclease 1 | NM_004111 |
| FOXM1 | Forkhead box M1 | U74512 |
| KIF20A | Kinesin family member 20A | NM_005733 |

TABLE 1-continued

| Gene Symbol | Gene Name | GENBANK Accession No. |
|---|---|---|
| MAD2L1 | MAD2 mitotic arrest deficient-like 1 | NM_002358 |
| MELK | Maternal embryonic leucine zipper kinase | NM_014791 |
| MLF1IP | MLF1 interacting protein | AA921830 |
| NUSAP1 | Nucleolar and spindle associated protein 1 | NM_016359 |
| PBX1 | Pre-B-cell leukemia homeobox 1 | NM_002585 |
| PRC1 | Protein regulator of cytokinesis 1 | NM_003981 |
| RACGAP1 | Rac GTPase activating protein 1 | NM_013277 |
| RAD54L | RAD54-like 2 | NM_003579 |
| RFC4 | Replication factor C (activator 1) 4, 37 kDa | NM_002916 |
| RRM2 | Ribonucleotide reductase M2 polypeptide | NM_001034 |
| TACC3 | Transforming, acidic coiled-coil containing protein | NM_006342 |
| TOP2A | Topoisomerase (DNA) II alpha 170 kDa | NM_001067 |
| TROAP | Trophinin associated protein (tastin) | NM_005480 |
| UBE2C | Ubiquitin-conjugating enzyme E2C | NM_007019 |

This list was shown to efficiently discriminate metastasis (Table 2), recurrence (Table 3) and survival (Table 4) when screened against a large panel of annotated ERα-positive breast cancer patients.

TABLE 2

| Gene Symbol | P-value | Fold Change |
|---|---|---|
| AURKA | 1.36E-4 | 1.93 |
| AURKB | 3.22E-5 | 1.84 |
| BUB1 | 5.52E-5 | 2.08 |
| CCNB1 | 4.75E-4 | 1.86 |
| CDCA3 | 1.70E-4 | 2.07 |
| CDKN3 | 0.002 | 1.76 |
| CEP55 | 7.78E-5 | 2.29 |
| DLGAP5 | 1.93E-4 | 2.19 |
| FEN1 | 0.001 | 1.48 |
| FOXM1 | 2.53E-5 | 2.63 |
| KIF20A | 4.74E-6 | 2.00 |
| MAD2L1 | 2.70E-4 | 1.99 |
| MELK | 1.48E-5 | 3.04 |
| MLF1IP | 0.003 | 1.52 |
| NUSAP1 | 3.21E-5 | 1.89 |
| PBX1 | 0.606 | −1.08 |
| PRC1 | 2.78E-5 | 2.37 |
| RACGAP1 | 3.31E-5 | 1.79 |
| RAD54L | 0.017 | 1.78 |
| RFC4 | 1.23E-4 | 1.72 |
| RRM2 | 3.56E-4 | 1.97 |
| TACC3 | 0.015 | 1.62 |
| TOP2A | 1.44E-5 | 3.02 |
| TROAP | 1.49E-6 | 1.82 |
| UBE2C | 6.96E-5 | 1.98 |

Data based on 200 samples: 171 with no metastatic event at 3 years, 19 with a metastatic event at 3 years. Expression of 12,624 genes was measured using a human genome U133A array.

TABLE 3

| Gene Symbol | P-value | Fold Change |
|---|---|---|
| AURKA | 1.55E-9 | 1.13 |
| AURKB | 9.92E-10 | 1.12 |
| BUB1 | 2.30E-7 | 1.13 |
| CCNB1 | 4.81E-6 | 1.11 |
| CDCA3 | 7.52E-9 | 1.14 |
| CDKN3 | 2.49E-5 | 1.06 |
| CEP55 | 5.97E-8 | 1.10 |
| DLGAP5 | 3.83E-5 | 1.08 |
| FEN1 | 5.27E-7 | 1.08 |
| FOXM1 | 2.34E-7 | 1.10 |
| KIF20A | 9.05E-8 | 1.14 |
| MAD2L1 | 4.35E-6 | 1.10 |
| MELK | 1.67E-6 | 1.10 |
| MLF1IP | 1.18E-5 | 1.10 |
| NUSAP1 | 3.55E-8 | 1.13 |
| PBX1 | 0.033 | 1.03 |
| PRC1 | 2.79E-10 | 1.15 |
| RACGAP1 | 9.73E-9 | 1.11 |
| RAD54L | 4.56E-7 | 1.10 |
| RFC4 | 6.61E-6 | 1.07 |
| RRM2 | 1.27E-8 | 1.16 |
| TACC3 | 4.14E-6 | 1.06 |
| TOP2A | 0.005 | 1.04 |
| TROAP | 3.17E-9 | 1.06 |
| UBE2C | 6.53E-9 | 1.14 |

Data based on 295 samples: 196 with no recurrence at 5 years, 91 with recurrence at 5 years. Expression of 14,719 genes was measured.

TABLE 4

| Gene Symbol | P-value | Fold Change |
|---|---|---|
| AURKA | 5.91E-7 | 1.13 |
| AURKB | 1.06E-7 | 1.13 |
| BUB1 | 1.94E-6 | 1.15 |
| CCNB1 | 2.68E-6 | 1.15 |
| CDCA3 | 1.04E-7 | 1.17 |
| CDKN3 | 2.02E-4 | 1.06 |
| CEP55 | 1.36E-5 | 1.10 |
| DLGAP5 | 5.11E-4 | 1.08 |
| FEN1 | 1.81E-5 | 1.09 |
| FOXM1 | 2.48E-6 | 1.12 |
| KIF20A | 6.71E-8 | 1.18 |
| MAD2L1 | 0.002 | 1.08 |
| MELK | 8.28E-6 | 1.11 |
| MLF1IP | 2.84E-4 | 1.09 |
| NUSAP1 | 5.81E-6 | 1.12 |
| PBX1 | 0.201 | 1.02 |
| PRC1 | 3.80E-8 | 1.14 |
| RACGAP1 | 3.03E-7 | 1.11 |
| RAD54L | 3.80E-6 | 1.12 |
| RFC4 | 7.93E-5 | 1.08 |
| RRM2 | 1.11E-5 | 1.07 |
| TACC3 | 7.03E-4 | 1.05 |
| TOP2A | 0.075 | 1.03 |
| TROAP | 2.11E-8 | 1.07 |
| UBE2C | 1.30E-7 | 1.15 |

Data based on 295 samples: 232 alive at 5 years, 48 deceased at 5 years. Expression of 14,719 genes was measured.

Given that this "cistrome signature" of 25 genes can stratify patients according to expected outcome, this signature is of use in identifying a priori breast cancer patients responsive to endocrine therapy treatment.

The data have shown that PBX1 has an important role in promoting endocrine therapy resistance in ERα-positive breast cancer. These data also suggest that expression of PBX1 can be used as a marker to discriminate breast cancer patients responsive to endocrine therapy a priori and with specificity. Therefore, in one embodiment, the present invention is a simple and novel method that can be used to identify patients that will respond to endocrine therapy. The method is based on the detection of PBX1 expression in ERα-positive breast cancer, where expression of PBX1 correlates with an increased likelihood of resistance to endocrine therapy. In this method of the invention, levels of gene expression are determined in a ERα-positive breast cancer tissue sample in vitro and compared with levels of gene expression in a control samples, e.g., a non-cancerous breast tissue sample. The presence of PBX1 expression at levels above levels seen in non-cancerous tissue is indicative of a poor prognosis for endocrine therapy treatment. The testing for gene expression in breast tissue samples can be performed either before initial breast cancer treatment begins or after endocrine therapy has begun. In this way, the method of the present invention can both be prognostic and diagnostic.

The present invention also relates to the use of gene expression patterns (or profiles or "signatures") which are clinically relevant to breast cancer. In particular, the identities of genes that are correlated with patient survival and breast cancer metastasis or recurrence are provided and referred to herein as the "cistrome signature" (Table 1). This gene expression profile, whether embodied in nucleic acid expression, protein expression, or other expression formats, may be used to predict survival of subjects afflicted with breast cancer and the likelihood of breast cancer metastasis or recurrence.

Therefore, the invention also provides for the use one or more than one of the genes of the cistrome signature to discriminate between breast cancer outcomes with significant accuracy. The genes of the cistrome signature were identified as being correlated with breast cancer outcomes such that the levels of their expression are relevant to a determination of the preferred treatment protocols for a patient. Thus, in one embodiment, the invention provides a method to determine the outcome of a subject afflicted with breast cancer, in particular ERα-positive breast cancer, by assaying a sample from said subject for expression of one or more than one of the genes of the cistrome signature. This method finds particular application in selecting an appropriate treatment regime for the patient.

In accordance with this method of the invention, the sample contains single cells or homogenous cell populations which have been dissected away from, or otherwise isolated or purified from, contaminating cells beyond that possible by a simple biopsy. Alternatively, undissected cells within a "section" of tissue may be used. Multiple means for such analysis are available, including detection of expression within an assay for global, or near global, gene expression in a sample (e.g. as part of a gene expression profiling analysis such as on a microarray) or by specific detection, such as quantitative PCR (Q-PCR), or real time quantitative PCR of one or more genes of the instant cistrome signature.

Preferably, the sample is isolated via non-invasive means. The expression of one or more genes of the instant cistrome signature in the sample may be determined and compared to the expression of said genes in a control, e.g., reference data of non-normal breast cells or alternatively expression levels in normal cells, preferably from the same sample or subject. In embodiments of the invention utilizing Q-PCR, the expression level may be compared to expression levels of reference genes in the same sample.

While good and poor outcomes may be defined relatively in comparison to each other, a "good" outcome may be viewed as a better than 50% survival rate after about 5 years post-treatment, absence of a metastatic event after about 3 years post-treatment, and/or absence of breast cancer recurrence after about 5 years post-treatment. A "poor" or "unfavorable" outcome may be viewed as a 50% or less survival rate after about 5 years post-treatment, presence of a metastatic event with about 3 years post-treatment, and/or presence of breast cancer recurrence within about 5 years post-treatment.

In addition to those already described, one of skill in the art would understand that tests for determining gene expression levels in vitro would include use of a variety of known assays described in the art. These assays would include but not be limited to microarray analysis of gene transcription profiles (Roepman P. 2009. *Clin. Cancer Res.* 15:7003-7011) and protein profiling using monoclonal antibodies immunocytochemistry (Sempere, L. F. et al. 2007. *Cancer Res.* 67:11612-11620).

The present invention also includes a kit containing a detection mechanism for determining the expression of one or more genes of the instant cistrome signature (see Table 1). A detection mechanism can be any standard comparison mechanism such as a microarray, which contains some or all of the markers of Table 1, or an assay, e.g., a reverse transcription polymerase chain reaction (RT-PCR), wherein the kit includes primers for amplifying some or all of the markers of Table 1. Primers for this type of analysis are routinely generated by the skilled artisan and can be designed using the nucleotide sequences disclosed herein.

In the context of the present invention, one of skill in the art would understand the type of endocrine therapies that might be used to treat patients and thus would be involved when using the methods of the present invention. Selective estrogen receptor modulators that could be used in patients would include but not be limited to tamoxifen, raloxifene, and toremifene, while aromatase inhibitors would include but be limited to anastrozole, exemestane, and letrozole.

The following non-limiting examples are provided to further illustrate the present invention.

EXAMPLE 1

Measurement of PBX1 Expression in Cells In Vitro

To measure PBX1 transcript in breast tumor cells, RT-qPCR analysis will be used. Breast cancer tissue biopsy samples will be excised surgically and immediately stored in liquid nitrogen until processing. Biopsy samples will be pulverized and total RNAs will be extracted using RNeasy microcolumns (Qiagen). RNA quality will be assessed using an Agilent Bioanalyser 2100 (Agilent Technologies, Santa Clara, Calif., USA). 500 ng of total RNAs will be reverse transcribed using iSCRIPT reverse transcriptase kit (Bio-Rad). All cDNA amplifications will be performed using 1/20th of the reverse transcription products and the IQ SYBR Green kit (Biorad), in the presence of 0.2 uM of each PBX1 primer. Quantitative PCR will be run on a CFX96 real time detection instrument (BioRad) with the following parameters: 5 min at 95° C. for the initial denaturation step, followed by 30 sec at 95° C., 30 sec at 60° C. and 30 sec at 72° C. per cycle for a total of 40 cycles. The PBX1 primers are as follows (PBX1 forward 5'-GAG GAA GCA GGA CAT TGG AG-3' (SEQ ID NO:1); PBX1 reverse 5'-AGG CTT CAT TCT GTG GCA GT-3' (SEQ ID NO:2)) for amplification of a 95-bp fragment and were designed using the Primer3 software. The amplified cDNA concentration will be evaluated using an external curve of standard samples and specific amplification will be checked using a melting curve. The PBX1 target concentration will be expressed relative to the concentration of the 28 sec house-keeping gene (Berthier et al. 2010. Br. J. Cancer 102:1024-1031. To detect PBX1 protein in breast cancer, immunocytochemistry will be used. PBX1 will be detected in immersion fixed paraffin-embedded sections of human breast cancer tissue using Human PBX1 Antigen Affinity-purified Monoclonal Antibody (Abnova, PBX1 monoclonal antibody (M01), clone 4A2) at 3 µg/mL overnight at 4° C. Before incubation with the primary antibody, tissue will subjected to heat-induced epitope retrieval using Antigen Retrieval. Tissue will be stained using the Anti-mouse HRP-DAB (Brown) and counterstained with hematoxylin (blue). Staining will be assessed with a Quick Score scheme where both the proportion of cells and the intensity of staining will be assessed (signal: 0=no signal, 1=weak signal, 2=intermediate signal, 3=strong signal; percentage: 0=0%, 1=<30%, 2=>30%).

What is claimed is:

1. A kit for determining outcome of a patient with breast cancer comprising
   (a) at least one PBX1 oligonucleotide selected from the group of SEQ ID NO:1 and SEQ ID NO:2; and
   (b) a detection mechanism for one or more genes selected from the group of AURKA, AURKB, BUB1, CCNB1, CDCA3, CDKN3, CEP55, DLGAP5, FEN1, FOXM1, KIF20A, MAD2L1, MELK, MLF1IP, NUSAP1, PRC1, RACGAP1, RAD54L, RFC4, RRM2, TACC3, TOP2A, TROAP and UBE2C.

* * * * *